(12) United States Patent
Franz et al.

(10) Patent No.: US 11,523,625 B2
(45) Date of Patent: Dec. 13, 2022

(54) FEED SUPPLEMENT BOLUS WITH ACTIVE YEAST

(71) Applicant: TECHMIX, LLC, Stewart, MN (US)

(72) Inventors: Peter H. Franz, Edina, MN (US); Marty J. Nelson, Scottsdale, AZ (US); Michael L. Nelson, Waconia, MN (US); Bradley Welding Kolstad, Waconia, MN (US); Nathan C. Upah, Clutier, IA (US); David J. Muysson, Minnetonka, MN (US); Dennis M. McKilligan, Ames, IA (US)

(73) Assignee: TechMix, LLC, Stewart, MN (US)

( * ) Notice: Subject to any disclaimer, the term of this patent is extended or adjusted under 35 U.S.C. 154(b) by 276 days.

(21) Appl. No.: 15/670,285

(22) Filed: Aug. 7, 2017

(65) Prior Publication Data

US 2019/0037884 A1    Feb. 7, 2019

(51) Int. Cl.
| | |
|---|---|
| *A23K 10/18* | (2016.01) |
| *A23K 50/10* | (2016.01) |
| *A61K 36/06* | (2006.01) |
| *C12N 1/16* | (2006.01) |
| *C12N 13/00* | (2006.01) |

(52) U.S. Cl.
CPC .............. *A23K 10/18* (2016.05); *A23K 50/10* (2016.05); *A61K 36/06* (2013.01); *C12N 1/16* (2013.01); *C12N 13/00* (2013.01)

(58) Field of Classification Search
CPC ........ A23K 10/18; A23K 50/10; A61K 36/06; C12N 1/16; C12N 11/00–04
See application file for complete search history.

(56) References Cited

U.S. PATENT DOCUMENTS

| | | |
|---|---|---|
| 3,843,800 A | 10/1974 | Langejan |
| 5,922,342 A | 7/1999 | Shah et al. |
| 7,157,258 B2 | 1/2007 | Durand et al. |
| 2010/0303778 A1 | 12/2010 | Simon et al. |
| 2013/0344005 A1* | 12/2013 | Le Jean ............... A61K 31/194 424/44 |
| 2016/0058700 A1 | 3/2016 | Laza-Knoerr et al. |
| 2016/0058760 A1 | 3/2016 | Singh et al. |

FOREIGN PATENT DOCUMENTS

| | | |
|---|---|---|
| CN | 102114112 | 7/2011 |
| DE | 20 2009 002 804 | 8/2010 |
| EP | 2099898 | 6/2017 |
| WO | 200168808 | 9/2001 |
| WO | 2007/038320 | 4/2007 |
| WO | 2010/125516 | 11/2010 |
| WO | WO2012017363 | 9/2012 |

OTHER PUBLICATIONS

Abd-Talib et al. "Survival of encapsulated probiotics through spray drying and non-refrigerated storage for animal feeds application" Agricultural Sciences 04(05)78-83 • Jan. 2013 (Year: 2013).*
English Translation of WO 2012017363, Cherry et al. 50 pgs completed Jun. 2019 (Year: 2019).*
Sniegowski et al. "*Saccharomyces cerevisiae* and *Saccharomyces paradoxus* coexist in a natural woodland site in North America and display different levels of reproductive isolation from European conspecics" FEMS Yeast Research 1 (2002) 299-306 (Year: 2002).*
"Acidogenic" Merriam-Webster Medical Dictionary, 1 pg accessed Mar. 23, 2021 (Year: 2021).*
Compendium of Veterinary Products—YMCP Vitali Bolus (TECHMIX) 2 pages 2022 (Year: 2022).*
Notification of Transmittal of the International Search Report and Written Opinion of the International Searching Authority or the Declaration, dated Jun. 27, 2018.
Horst, E.A., et al.; "Effects of maintaining eucalcemia following immunoactivation in lactating Holstein dairy cows" American Dairy Science Association; Jan. 27, 2020; J. Dairy Sci. 103:7472-7486; Elsevier Inc. and Fass Inc.; Ames, IA.
Al-Qaisi, Mohmmad, et al.; "Effects of an oral supplement containing calcium and live yeast on post-absorptive metabolism, inflammation and production following intravenous lipopolysaccharide infusion in dairy cows"; Research in Veterinary Science; Jan. 7, 2020; 129 (2020) 74-81; Elsevier Ltd., Ames, IA.
TECHMIX; "YMCP Vitall bolus"; Powerpoint Presentation 2020.

\* cited by examiner

*Primary Examiner* — Thane Underdahl
(74) *Attorney, Agent, or Firm* — DeWitt LLP

(57) ABSTRACT

A ruminant dietary supplement in the form of a pressed shelf-stable solid pill or bolus that effervesces when administered into the reticulum of a ruminant and releases calcium and dried active yeast.

16 Claims, No Drawings

FEED SUPPLEMENT BOLUS WITH ACTIVE YEAST

CROSS-REFERENCED TO RELATED APPLICATIONS

Not applicable

STATEMENT REGARDING FEDERALLY SPONSORED RESEARCH OR DEVELOPMENT

Not applicable

BACKGROUND OF THE INVENTION

I. Field of the Invention

The present invention relates generally to a feed supplement preparation for administration to ruminant animals and, more particularly, to a solid tablet or bolus that provides an effervescent release of calcium and dried active yeast into the reticulum of large ruminants for the prevention or treatment of hypocalcemia and to provide a positive increase in additional dietary supplement materials.

II. Related Art

It is known to administer several essential nutrients required by lactating cows following parturition. Prevention of low blood calcium, commonly referred to as hypocalcemia, is of great concern to the producer. Because of the calcium required for colostrogenesis and subsequent lactogenesis, the requirement for calcium increases greatly during the periparturient period. Clinical hypocalcemia is characterized by a blood calcium concentration drop below a critical threshold resulting in a potentially life threatening state of recumbency. Solid boluses containing calcium chloride have been produced and administered to animals orally. The bolus may also contain acid and base ingredients which react to effervesce in the reticulum of the animal. One such bolus is described in U.S. Patent Publication No. 2016/0058760 A1.

Another acute problem associated with cows is that in the days leading up to parturition their dry matter intake decreases, in some cases profoundly. As selection for higher producing genetics continues to be emphasized the severity of this periparturient dry matter intake suppression becomes of greater consequence. Dry matter intake reduction of 20-25% in the first 24-48 hours after calving is common, independent of calcium status. Should the dry matter intake not increase in concert with milk production the fresh cow is at an increased risk for hypocalcemia (milk fever), displaced abomasum, ketosis, and poor lactational performance. Dry matter intake and nutrient absorption following calving are also influenced by the transition of the rumen microflora to a diet greater in carbohydrate content, specifically rapidly fermentable starch, and lower in fiber than they were exposed to prepartum. To rapidly foster the growth and prefoliation of starch digesting bacteria in accordance with energetic demands there is a need for a dietary supplement that acts as food for these bacteria and ultimately enables the cow to maintain a higher level of dry matter feed intake and resulting in more available energy to support lactation in the immediate period after calving.

SUMMARY OF THE INVENTION

By means of the present invention, there is provided a unique formulation for a bovine supplement for fresh cows that delivers calcium chloride, calcium carbonate, magnesium, potassium and other electrolytes in a stable pressed solid bolus form which also contains dried live active yeast. The successful incorporation of dried stable active yeast in the formulation in which the yeast remains active in a shelf-stable compressed dry bolus dosage form greatly enhances the effectiveness of the supplement. The formulation also includes sufficient amounts of acidic and basic components which react to generate a gas release in an aqueous medium to accomplish effervescent release of calcium and dried active yeast into the reticulum via a solid bolus dosage form.

DETAILED DESCRIPTION

The present invention provides a unique formulation for a bovine supplement to be administered to fresh cows that delivers calcium chloride, calcium carbonate, magnesium, potassium and other beneficial constituents in an anhydrous pressed solid bolus dosage form and which also contains dried live active yeast. The successful incorporation of live active yeast which remains stable in a pressed bolus has greatly enhanced the effectiveness of the supplement.

It has been found that administering ruminant supplements containing large amounts of calcium is more successful if a stable pressed solid bolus is used so that the animal swallows the bolus whole into the fluid in the reticulum where it dissolves and reacts. Effervescent release of calcium has also been found to be very effective.

The present invention further has successfully added dried stable active yeast to an anhydrous pressed solid bolus dosage form. Thus, the supplement not only provides needed calcium, but it also produces a previously undocumented positive increase in dry matter feed intake and milk production. In this manner, the supplement treats the two biggest problems encountered by cows right after calving—low blood calcium and low feed intake and demonstrates direct economic benefit from treatment. It is believed that the yeast successfully enhances microbial action stimulating rumen fermentation.

The yeast is in the form of micro-granules of dehydrated yeast coated with a homogeneous hydrophobic substance such as a fat or fatty acid that stabilizes the yeast against physical and chemical stresses including heat and compression. Such a yeast form is available from Lallemand S. A. of Blagnac, France.

One successful combination had the following range of ingredients.
Product Ingredients (wt)

| INGREDIENT | MIN % | MAX % | ABOUT |
|---|---|---|---|
| Calcium Chloride | 30.000% | 70.000% | |
| Calcium Carbonate | 5.000% | 25.000% | |
| Sugar Alcohol | 10.000% | 30.000% | |
| Organic Acid | | | 5.000% |
| Potassium Chloride | 2.300% | 15.000% | |
| Niacin RP | | | 3.000% |
| Live Yeast | 1.000% | 5.000% | |
| Magnesium Sulfate | 1.000% | 5.000% | |
| Vitamin E | | | 0.050% |
| Betaine HCL | 0.025% | 1.000% | |
| Zinc Sulfate | | | 0.050% |
| Magnesium Stearate | 0.500% | 2.000% | |

The sugar alcohol is selected from sorbitol, maltitol, erythritol, mannitol, and combinations thereof. The acid constituent, which reacts with the carbonate to provide an effervescence is selected from citric acid, sorbic acid, formic acid and combinations thereof.

One example of a successful product has about 2-3% live yeast, about 8% calcium carbonate and about 60% calcium chloride. The formula may contain varying amounts of dried live active yeast between 1% and 5% with 2%-3% being typical. A typical dose is 2-110 g solid boluses.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A ruminant dietary supplement in the form of a pressed shelf-stable solid pill or bolus administered into the reticulo-rumen of a ruminant animal, comprising;
   (a) at least 30% wt of an acidogenic source of calcium; and
   (b) particles of dried live active yeast coated with a hydrophobic fat or fatty acid substance with the coating of the hydrophobic fat or fatty acid material separate from the dried live active yeast particles prior to and during the material being sprayed around the exterior of the dried live active yeast particles;
   (c) wherein the hydrophobic fat or fatty acid coating contributes to a reduction in the degradation of cells in the yeast particles and enables them to remain viable when the yeast particles are homogeneously incorporated into the pressed solid pill or bolus.

2. The ruminant dietary supplement of claim 1, wherein the amount of dried live active yeast is about 1-5% wt of the pill or bolus.

3. The ruminant dietary supplement of claim 2, wherein the amount of dried live active yeast is about 2-3% wt of the pill or bolus.

4. The ruminant dietary supplement of claim 1 further comprising an acid constituent and a base constituent.

5. The ruminant dietary supplement of claim 4, wherein the acid constituent comprises citric acid, sorbic acid, formic acid, or combinations thereof.

6. The ruminant dietary supplement of claim 4, wherein the base constituent comprises calcium carbonate.

7. The ruminant dietary supplement of claim 1, wherein the acidogenic calcium source comprises calcium chloride.

8. The ruminant dietary supplement of claim 1 further comprising one or more minerals within the solid pressed pill or bolus.

9. The ruminant dietary supplement of claim 8, wherein the one or more minerals comprise magnesium, potassium, zinc, or combinations thereof.

10. The ruminant dietary supplement of claim 1 further comprising a sugar alcohol within the solid pressed pill or bolus.

11. The ruminant dietary supplement of claim 10, wherein the sugar alcohol comprises sorbitol, maltitol, erythritol, mannitol, or combinations thereof.

12. The ruminant dietary supplement of claim 1, wherein the ruminant animal comprises a cow, sheep, goat, deer, giraffe, or camel.

13. A ruminant dietary supplement in the form of a pressed shelf-stable solid pill or bolus administered into the reticulo-rumen of a ruminant animal, comprising about 2-3% wt particles of dried live active yeast, about 8% wt calcium carbonate, an acidogenic source of calcium in the form of about 60% wt calcium chloride and about 5% wt of an acid constituent for producing effervescence within the reticulo-rumen of the ruminant animal when the solid pill or bolus is swallowed.

14. A ruminant dietary supplement as in claim 13, wherein the acid constituent comprises citric acid, sorbic acid, formic acid, or combinations thereof.

15. The ruminant dietary supplement of claim 13 further comprising a coating formed from a hydrophobic fat or fatty acid substance around the particles of dried live active yeast with the coating of the hydrophobic fat or fatty acid material separate from the dried live active yeast particles prior to and during the material being sprayed around the exterior of the dried live active yeast particles, said coating contributing to a reduction in the degradation of the cells in the dried live active yeast particles and enabling them to remain viable when the dried live active yeast particles are homogeneously incorporated into the pressed solid pill or bolus.

16. The ruminant dietary supplement of claim 13, wherein the ruminant animal comprises a cow, sheep, goat, deer, giraffe, or camel.

* * * * *